(12) United States Patent
Zhou et al.

(10) Patent No.: US 12,419,710 B2
(45) Date of Patent: Sep. 23, 2025

(54) ELASTIC GATHERED AUTOMATICALLY CENTERING PANEL CLAMPING MECHANICAL FINGERS FOR VASCULAR INTERVENTION

(71) Applicant: SHANGHAI OPERATION ROBOT CO., LTD., Shanghai (CN)

(72) Inventors: Guanlin Zhou, Shanghai (CN); Daozhi Liu, Shanghai (CN); Yikun Liu, Shanghai (CN); Dong Liu, Shanghai (CN)

(73) Assignee: SHANGHAI OPERATION ROBOT CO., LTD., Shanghai (CN)

( * ) Notice: Subject to any disclaimer, the term of this patent is extended or adjusted under 35 U.S.C. 154(b) by 421 days.

(21) Appl. No.: 17/912,488

(22) PCT Filed: Apr. 7, 2020

(86) PCT No.: PCT/CN2020/083458
§ 371 (c)(1),
(2) Date: Sep. 16, 2022

(87) PCT Pub. No.: WO2021/184443
PCT Pub. Date: Sep. 23, 2021

(65) Prior Publication Data
US 2023/0142137 A1    May 11, 2023

(30) Foreign Application Priority Data
Mar. 17, 2020    (CN) .......................... 202010188608.7

(51) Int. Cl.
*A61B 34/35*    (2016.01)
(52) U.S. Cl.
CPC .................... *A61B 34/35* (2016.02)

(58) Field of Classification Search
CPC ......... A61B 34/35; A61B 34/37; A61B 34/30; A61B 90/57; A61B 2034/301; A61B 34/70; A61B 2034/303
(Continued)

(56) References Cited

U.S. PATENT DOCUMENTS

2016/0354582 A1    12/2016  Yu et al.
2017/0189128 A1*    7/2017  Auld ...................... A61B 34/30
(Continued)

FOREIGN PATENT DOCUMENTS

CN           1843713 A      10/2006
CN        100368158 C  *    2/2008
(Continued)

*Primary Examiner* — Kira Nguyen
(74) *Attorney, Agent, or Firm* — Bayramoglu Law Offices LLC

(57) ABSTRACT

Mechanical fingers for clamping catheters, guild wires, and the like equipment for vascular intervention include a left clamping panel, a right clamping panel, left gathering pieces, right gathering pieces, a linear-propelling mechanism, and a frame. The linear-propelling mechanism is arranged on the frame. The left clamping panel and the right clamping panel are oppositely arranged, and are each arranged on the linear-propelling mechanism. The left gathering pieces and the right gathering pieces are arranged on the left clamping panel and the right clamping panel, respectively. The linear-propelling mechanism drives the left clamping panel and the right clamping panel to move towards or move away from each other. The mechanical fingers can realize adaptive clamping for intervening equipment in a widely varying diameter range. The clamping surfaces of panels in the mechanical fingers are provided with grid-and-stripe microstructures and are made from resilient materials.

10 Claims, 2 Drawing Sheets

(58) Field of Classification Search
USPC .......................................................... 700/245
See application file for complete search history.

(56) References Cited

U.S. PATENT DOCUMENTS

2023/0355261 A1* 11/2023 Yu ........................... A61B 34/30
2024/0277370 A1* 8/2024 Lazzari ................. A61B 34/37

FOREIGN PATENT DOCUMENTS

| CN | 102785251 | A |   | 11/2012 |
|----|-----------|---|---|---------|
| CN | 103433929 | A |   | 12/2013 |
| CN | 104644270 | A |   | 5/2015  |
| CN | 107049499 | A |   | 8/2017  |
| CN | 107106155 | A |   | 8/2017  |
| CN | 107320181 | A | * | 11/2017 |
| CN | 109199590 | A |   | 1/2019  |
| CN | 110327116 | A |   | 10/2019 |
| JP | S59151687 | U |   | 10/1984 |
| JP | S61201790 | U |   | 12/1986 |
| JP | 2017042907 | A |  | 3/2017  |
| WO | 2014068563 | A1 | | 5/2014  |

\* cited by examiner

ELASTIC GATHERED AUTOMATICALLY CENTERING PANEL CLAMPING MECHANICAL FINGERS FOR VASCULAR INTERVENTION

CROSS REFERENCE TO THE RELATED APPLICATIONS

This application is the national phase entry of International Application No. PCT/CN2020/083458, filed on Apr. 7, 2020, which is based upon and claims priority to Chinese Patent Application No. 202010188608.7, filed on Mar. 17, 2020, the entire contents of which are incorporated herein by reference.

TECHNICAL FIELD

The present invention relates to a field of the medical equipment, particularly to elastic gathered automatically centering panel clamping mechanical fingers for vascular intervention.

BACKGROUND

A vascular interventional robot is a master-slave teleoperated robot system that allows physicians to avoid radiation damage and to achieve precise operations. The master hand of master-slave interventional robot sends action commands from a physician, such as clamping, pushing, and rotating a device, and the slave hand is responsible for achieving these actions. Among them, the clamping of the device is a very important part. When the physician manipulates the device, he or she first configures the fingers to hold the device, and then rotates, or push it. The clamping mechanical fingers are often configured in a two-finger mechanical hand, which must ensure that the device is held with an appropriate force. If the force is too large, it may lead to damage to the surface of the device. If the force is too small, the device might slip in operation. In addition, there are also technical challenges that the clamping fingers is required to be compatible with thousands of devices which are on the current market and has been successfully promoted clinically.

At present, the device clamping method of vascular interventional robots basically is a two roller-to-press or a two planar track-to-press method, such as the products of Catheter Robotics (France) and CorPath (USA). The biggest problem is that these clamping methods are hardly compatible with the various interventional devices currently available in the market, and even require robotic-specific devices, which greatly limits the usage of vascular interventional robots. In China, Institute of Automation of Chinese Academy of Sciences has adopted a roller-to-roll method for clamping, and the Beijing Institute of Technology has developed a gear-extrusion type of catheter and guidewire clamping method, which requires the device to pass through a special enclosed channel.

Based on various sources, a conclusion can be made that the method for clamping the interventional devices of a vascular interventional robot so far has a lot of urgent problems to be solved. Firstly, the clamping fingers must have good compatibility for a range from a smallest catheter and guidewire to a handle for a large stent, and the good compatibility will enhance versatility of the robot. Additionally, in order to facilitate the placement of devices, the clamping fingers should preferably be open type instead of closed type. Furthermore, since a plurality of clamping fingers are often required in a surgery and the centering capability ensures the coaxiality of multiple devices in use, the clamping fingers must be able to perform automatically centering, that is, the center point of the device stays constant before and after replacement of different devices. Finally, front ends of the clamping fingers must be designed to be easily removable and can be discarded or sterilized for reuse after a single use, to meet the cleanliness requirements of clinical surgeries.

A patent (application No. 201710414380.7) discloses a teleoperation vascular interventional operation robot system and method which includes a lifting portion, a near-end operation portion and a far-end operation portion. The near-end operation portion is arranged on the lifting portion; the far-end operation portion is used for driving the near-end operation portion; the near-end operation portion can move or rotate inside the three-dimensional space. The teleoperation vascular interventional operation robot system and method has the advantages that the structure is compact, the operation mobility is high, and the operation requirement of common clinic interventional operation is met; a mechanical hand is controlled through the far-end operation portion for performing the operation, the operation is flexible and precise, and the interventional operation quality is improved; the mechanical hand is controlled by the far-end operation portion for performing the operation, doctors of an intervention department are liberated from the radial environment, and accumulated radial injuries are reduced. However, the above-mention patent is complicated to operate and has low compatibility.

SUMMARY

To address the defects in the prior art, the present invention provides elastic gathered automatically centering panel clamping mechanical fingers for vascular intervention.

In the present invention, the elastic gathered centering panel clamping mechanical fingers for vascular intervention include a left clamping panel, a right clamping panel, left gathering pieces, right gathering pieces, a linear-propelling mechanism, and a frame.

the linear-propelling mechanism is arranged on the frame.

The left clamping panel and the right clamping panel are oppositely arranged, and are each arranged on the linear-propelling mechanism.

The left gathering pieces and the right gathering pieces are arranged on the left clamping panel and the right clamping panel, respectively.

The linear-propelling mechanism drives the left clamping panel and the right clamping panel to move towards or move away from each other.

Preferably, the left gathering pieces are arranged on two sides of the left clamping panel, and the right gathering pieces are arranged on two sides of the right clamping panel. Clamping surfaces of the left gathering pieces and the right gathering pieces are arranged to face each other.

Preferably, the linear-propelling mechanism includes a driving electric motor, position-limiting guiding rails, adjusting screw rods, and moving assemblies.

The moving assemblies are provided with position-limiting holes and spiral holes, and axial directions of the position-limiting holes and the spiral holes are the same.

The position-limiting guiding rails and the adjusting screw rods are arranged in the position-limiting holes and the spiral holes, respectively.

The adjusting screw rods drive the moving assemblies to move reciprocally on the position-limiting guiding rails by rotating motions.

An output end of the driving electric motor and one ends of the adjusting screw rods are engaged by cogwheels. The driving electric motor drives to the adjusting screw rods to rotate by the cogwheels.

Preferably, two of the position-limiting guiding rails, two of the adjusting screw rods, and two of the moving assemblies are arranged.

The left clamping panel and the right clamping panel are arranged on one of the moving assemblies, respectively.

Preferably, the moving assemblies are each provided with a position-limiting block, and a bottom of each of the left clamping panel and the right clamping panel is provided with an installing slot. The left clamping panel and the right clamping panel insert into the installing slots by the position-limiting blocks, to be arranged on the moving assemblies.

Preferably, an upper end of the position-limiting block is provided with resilient locking pieces. The interior wall of the installing slot is provided with position-limiting through-holes. When the position-limiting block is inserted into the installing slot, the resilient locking pieces clamp into the position-limiting through-holes to realize the fixed connection between moving assemblies and the left clamping panel or the right clamping panel.

Preferably, further including the unlocking tool. The unlocking tool can extend into the position-limiting through-holes and push the resilient locking pieces away from the position-limiting through-holes.

Preferably, the frame includes a bottom board and parallel sideboards arranged on two sides of the bottom board, and each of the position-limiting guiding rails and the adjusting screw rods is arranged on the sideboards arranged on the two sides of the bottom board.

Preferably, the clamping surfaces of the left gathering pieces and the right gathering pieces are clamping surfaces resiliently arranged.

Preferably, the clamping surfaces of the left gathering pieces and the right gathering pieces are provided with stripes.

Compared to the prior arts, the present invention has the following advantages.

1. The present invention can realize adaptive clamping for intervening equipment in a widely varying diameter range. It is compatible with the current intervening equipment clinically used, and has characteristics such as a high-performance, strong versatility, and a compact structure.
2. In the present invention, the clamping surfaces are provided with grid-and-stripe microstructures, are made from resilient materials, and safely and reliably clamp the intervening equipment without damages.
3. The present invention centers the equipment by V-shaped resilient gathering pieces. The clamping center is immobile relative to the clamping panels, and the clamping center will not vary for different equipment with different diameters, allowing guild wires to be easily operated in catheters.
4. The clamping panel of the present invention is removable, which can be discarded in clinical use and facilitates aseptic cleaning or sterilization.

BRIEF DESCRIPTION OF THE DRAWINGS

By reading the detailed description of the non-restrictive embodiments with reference to the following drawings, other features, purposes, and advantages of the present invention will be more obvious.

Figure 1:
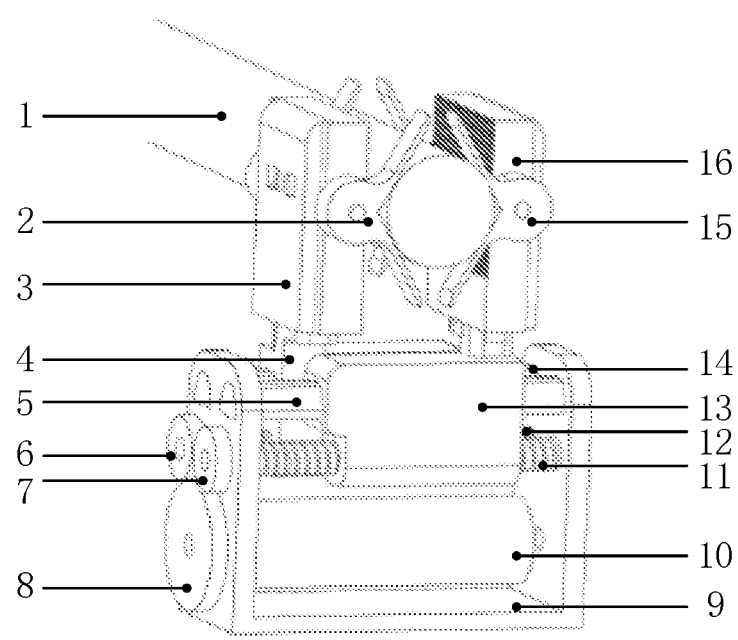
FIG. 1 is a structural schematic diagram of the present invention.

THE REFERENCE NUMERALS intervening equipment 1
left gathering piece 2
left clamping panel 3
unlocking tool 301
reset spring 302
resilient locking piece 303
back moving assembly 4
front guiding rail 5
back cogwheel 6
front cogwheel 7
electric motor cogwheel 8
frame 9
electric motor 10
front screw rod 11
back screw rod 12
front moving assembly 13
back guiding rail 14
right gathering piece 15
right clamping panel 16

DETAILED DESCRIPTION OF THE EMBODIMENTS

As follows, the present invention is described in detail in conjunction with specific embodiments. The following embodiments help the skilled in the art to further understand the present invention, but do not limit it in any way. It should be noted that to a person of ordinary skill in the art, a number of variations and improvements can be made without departing from the ideas of the present invention. These shall fall within the scope of protection of the present invention.

Figure 2:
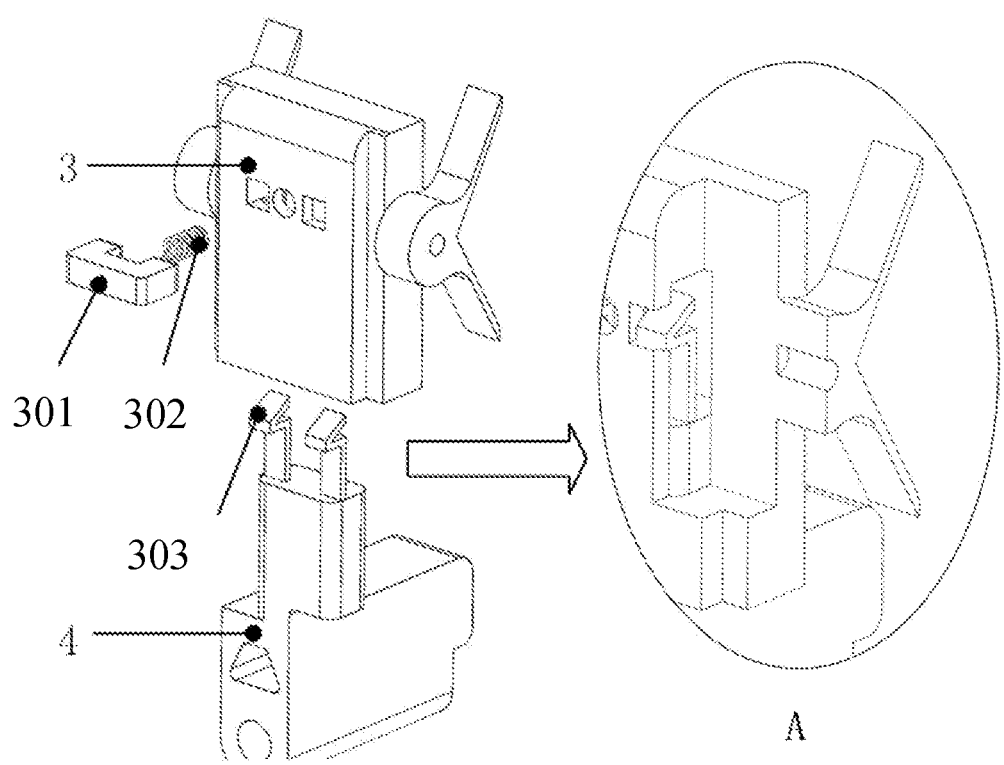
FIG. 2 is a schematic diagram showing an internal structure of a panel during disassembly and assembly of the present invention.

As shown in FIG. 1 and FIG. 2, the present invention provides elastic gathered automatically centering panel clamping mechanical fingers for vascular intervention. The mechanical fingers include the left gathering pieces 2, the left clamping panel 3, the right gathering pieces 15, the right clamping panel 16, the frame 9, and a linear-propelling mechanism. The linear-propelling mechanism includes the front screw rod 11, the front moving assembly 13, the front guiding rail 5, the front cogwheel 7, the back screw rod 12, the back moving assembly 4, the back guiding rail 14, the back cogwheel 6, the electric motor cogwheel 8, and the electric motor 10. As shown in FIG. 1, the front direction in the present invention refers to the direction perpendicular to the paper and pointing outwards, and the back direction in the present invention refers to the direction perpendicular to the paper and pointing inwards. The linear-propelling mechanism is arranged on the frame 9. The frame 9 includes a bottom board and parallel sideboards separately arranged on two sides of the bottom board, and the front guiding rail 5, the front screw rod 11, the back guiding rail 14, and the back screw rod 12 are all arranged on the sideboards on the two sides of the bottom board. One pair of the left gathering pieces 2 are arranged on the front side and back side of the left clamping panel 3, respectively. The left clamping panel 3 is arranged on the back moving assembly 4. The back moving assembly 4 and the back screw rod 12 are screwed and fitted with each other, and scotched by the back guiding rail 14. The back cogwheel 6 is fixedly arranged on one end of the back screw rod 12. The right gathering pieces 15 are separately arranged on sides of the right clamping panel 16. The right clamping panel 16 is arranged on the front moving assembly 13. The front moving assembly 13 and the front screw rod 11 are screwed and fitted with each other, and scotched by the front guiding rail 5. The front cogwheel 7 is arranged on one end of the front screw rod 11. The design method that separates the arrangements of the back moving assembly 4 and the front moving assembly 13 ensures that each of the back moving assembly 4 and the front moving assembly 13 has a comparatively longer length, avoiding motional stagnation caused by pulling and pressing the intervening equipment 1.

Further, the left clamping panel 3 and the right clamping panel 16 moves towards each other to clamp the intervening equipment 1, and the left gathering pieces 2 and the right gathering pieces 15 have V-shaped structures for gathering and automatically centering the intervening equipment 1. Under the condition that the diameter of the intervening equipment 1 is quite small, the left gathering pieces 2 and the right gathering pieces 15 press each other, which can be deformed to be at an equal level with clamping surfaces of the left clamping panel 3 and the right clamping panel 16. The clamping surfaces of the left clamping panel 3 and the right clamping panel 16 are arranged to be resilient clamping surfaces, and the clamping surfaces flexibly contact the intervening equipment 1 to avoid damage. Additionally, the clamping surfaces are embossed with grids to increase friction and to avoid slipping.

Further, the front moving assembly 13 has the same structure as the back moving assembly 4. The back moving assembly 4 is taken as an example for demonstration. The back moving assembly 4 is provided with a position-limiting block. The bottom of the left clamping panel 3 is arranged with an installing slot. The left clamping panel 3 inserts into the installing slot by the position-limiting block, to be arranged on the back moving assembly 4. The upper end of the position-limiting block is provided with the resilient locking pieces 303. The interior wall of the installing slot is provided with position-limiting through-holes. When the position-limiting block is inserted into the installing slot, the resilient locking pieces 303 clamp into the position-limiting through-holes to realize the fixed connection between the moving assemblies and the left clamping panel or the right clamping panel. The left clamping panel 3 is provided with the unlocking tool 301. The unlocking tool 301 can extend into the position-limiting through-holes and push the resilient locking pieces 303 away from the position-limiting through-holes. The reset spring 302 is configured to connect and fix the unlocking tool 301 to the left clamping panel 3. The left clamping panel 3 and the right clamping panel 16 are sterilized for reuse, or discarded as disposable consumables.

Further, the front cogwheel 7 and the back cogwheel 6 are engaged with the electric motor cogwheel 8 that is arranged on the output shaft of the electric motor 10 at the same time. The front screw rod 11 and the back screw rod 12 are parallelly arranged on the frame 9 with the threads of the two screw rods going inverse directions relative to each other. When the front cogwheel 7 and the back cogwheel 6 driving the screw rods is engaged with the electric motor cogwheel 8 of the electric motor 10 to rotate, the front screw rod 11 and the back screw rod 12 rotate in the same direction simultaneously, and the back moving assembly 4 and the front moving assembly 13 moves towards or away with each other simultaneously to realize centering clamping or loosening the intervening equipment 1.

As a varied embodiment, after the front cogwheel 7 and the back cogwheel 6 are engaged with each other, one of them engages with the electric motor cogwheel 8 on the output shaft of the electric motor 10, and threads of the front screw rod 11 and the back screw rod 12 go in the same direction.

By selecting the preferred embodiment as an example, the workflow of the present invention is demonstrated as follows. When the electric motor 10 rotates, the electric motor cogwheel 8 drives the front cogwheel 7 and the back cogwheel 6 to rotate in the same direction. Since the threads of the front screw rod 11 and the back screw rod 12 go inverse directions, the front moving assembly 13 and the back moving assembly 4 move simultaneously in inverse directions on the front guiding rail 5 and the back guiding rail 14. The front screw rod 11 and the back screw rod 12 are equal in screw pitch, and moving distance and velocity. When the left clamping panel 3 and the right clamping panel 16 are moving towards each other, the left gathering pieces 2 and the right gathering pieces 15 automatically center the intervening equipment 1. When they have moved to a certain distance, the objective of stably clamping is realized.

Specific embodiments of the present invention are described above. It should be understood that the present invention is not limited to the particular embodiments described above, and that the skilled in the art may make various variations or modifications within the scope of the claims, which do not affect the substance of the present invention. The embodiments and features in the embodiments of the present application can be combined randomly without conflictions.

What is claimed is:

1. Elastic gathered automatically centering panel clamping mechanical fingers for a vascular intervention, comprising a left clamping panel, a right clamping panel, left gathering pieces, right gathering pieces, a linear-propelling mechanism, and a frame, wherein the linear-propelling mechanism is arranged on the frame;

the left clamping panel and the right clamping panel are oppositely arranged, and the left clamping panel and the right clamping panel are each arranged on the linear-propelling mechanism;

the left gathering pieces are arranged on the left clamping panel, and the right gathering pieces are arranged on the right clamping panel; and the linear-propelling mechanism drives the left clamping panel and the right clamping panel to move towards each other, or the linear-propelling mechanism drives the left clamping panel and the right clamping panel to move away from each other, wherein the linear-propelling mechanism comprises position-limiting guiding rails, adjusting screw rods, and moving assemblies, and wherein each of the moving assemblies is provided with position-limiting holes and spiral holes; an axial direction of each of the position-limiting holes and an axial direction of each of the spiral holes is the same;

each of the position-limiting guiding rails is arranged in the position-limiting holes, and each of the adjusting screw rods is arranged in the spiral holes;

each of the adjusting screw rods drives each of the moving assemblies to move reciprocally on each of the position-limiting guiding rails by a rotating motion.

2. The mechanical fingers according to claim 1, wherein the left gathering pieces are arranged on two sides of the left clamping panel, respectively; the right gathering pieces are arranged on two sides of the right clamping panel, respectively; and clamping surfaces of each of the left gathering pieces and clamping surfaces of each of the right gathering pieces are arranged to face each other.

3. The mechanical fingers according to claim 1, wherein the linear-propelling mechanism comprises a driving electric motor, wherein
an output end of the driving electric motor and one end of each of the adjusting screw rods are engaged by a cogwheel; and the driving electric motor drives each of the adjusting screw rods to rotate by the cogwheel.

4. The mechanical fingers according to claim 3, wherein two of the position-limiting guiding rails are arranged, two of the adjusting screw rods are arranged, and two of the moving assemblies are arranged; and
the left clamping panel is arranged on a first moving assembly, and the right clamping panel is arranged on a second moving assembly.

5. The mechanical fingers according to claim 3, wherein a first moving assembly of the moving assemblies is provided with a first position-limiting block, and a second moving assembly of the moving assemblies is provided with a second position-limiting block; a bottom of the left clamping panel is provided with a first installing slot, and a bottom of the right clamping panel is provided with a second installing slot; and the left clamping panel inserts into the first installing slot by the first position-limiting block to be arranged on the first moving assembly, and the right clamping panel inserts into the second installing slot by the second position-limiting block to be arranged on the second moving assembly.

6. The mechanical fingers according to claim 5, wherein an upper end of the first position-limiting block is provided with a first resilient locking piece, and an upper end of the second position-limiting block is provided with a second resilient locking piece; an interior wall of the first installing slot is provided with a first position-limiting through-hole, and an interior wall of the second installing slot is provided with a second position-limiting through-hole; and when the first position-limiting block is inserted into the first installing slot, and the second position-limiting block is inserted into the second installing slot, the first resilient locking piece clamps into the first position-limiting through-hole, and the second resilient locking piece clamps into the second position-limiting through-hole to realize a fixed connection between the first moving assembly and the left clamping panel and a fixed connection between the second moving assembly and the right clamping panel.

7. The mechanical fingers according to claim 6, wherein the mechanical fingers further comprises an unlocking tool; and the unlocking tool is configured to extend into the first position-limiting through-hole and the second position-limiting through-hole to push the first resilient locking piece and the second resilient locking piece away from the first position-limiting through-hole and the second position-limiting through-hole, respectively.

8. The mechanical fingers according to claim 3, wherein the frame comprises a bottom board and parallel sideboards, wherein the parallel sideboards are arranged on two sides of the bottom board, respectively; and each of the position-limiting guiding rails and each of the adjusting screw rods are arranged on the parallel sideboards.

9. The mechanical fingers according to claim 1, wherein the clamping surfaces of each of the left gathering pieces and the clamping surfaces of each of the right gathering pieces are clamping surfaces resiliently arranged.

10. The mechanical fingers according to claim 1, wherein the clamping surfaces of each of the left gathering pieces and the clamping surfaces of each of the right gathering pieces are provided with stripes.

* * * * *